United States Patent [19]

Wahlberg et al.

[11] Patent Number: 4,629,452
[45] Date of Patent: Dec. 16, 1986

[54] ARRANGEMENT IN A CATHETER UNIT WITH ATTACHMENT WINGS, FOR INFUSION CANNULAS

[75] Inventors: Harry U. Wahlberg, Helsingboro; Kálmán Csiki, Landskrona, both of Sweden

[73] Assignee: Viggo AB, Helsingborg, Sweden

[21] Appl. No.: 640,903

[22] Filed: Aug. 15, 1984

[30] Foreign Application Priority Data

Aug. 29, 1983 [SE] Sweden .................................. 8304657

[51] Int. Cl.[4] .............................................. A61N 5/00
[52] U.S. Cl. ..................................... 604/177; 604/158; 604/164
[58] Field of Search ............... 604/177, 158, 164, 162, 604/163

[56] References Cited

U.S. PATENT DOCUMENTS

| | | | |
|---|---|---|---|
| 3,640,275 | 2/1972 | Burke et al. | 604/177 |
| 3,766,915 | 10/1973 | Rychlik | 604/163 |
| 3,782,283 | 1/1974 | Thompson et al. | 604/177 |
| 3,863,631 | 2/1975 | Baldwin | 604/177 |
| 3,910,272 | 10/1975 | Forberg | 604/162 |
| 4,353,369 | 10/1982 | Muetterties et al. | 604/164 |

Primary Examiner—C. Fred Rosenbaum
Assistant Examiner—Karen L. Kaechele
Attorney, Agent, or Firm—Beveridge, DeGrandi & Weilacher

[57] ABSTRACT

In a catheter unit for infusion cannulas, attachment wings are folded against the body portion of the catheter unit and laterally enclosed by a removable sleeve, a wall portion of which forms a finger grip for manipulation of the infusion cannula upon vein puncture.

12 Claims, 4 Drawing Figures

ARRANGEMENT IN A CATHETER UNIT WITH ATTACHMENT WINGS, FOR INFUSION CANNULAS

The present invention relates to an arrangement in a catheter unit with attachment wings, for infusion cannulas.

The catheter unit of infusion cannulas is frequently provided with a base plate consisting of laterally protruding wings which, after puncture of a vein by means of a puncture unit extending through the catheter unit, are fixed to the skin of the patient by means of, for example, strips of tape. Especially on small catheter units made of flexible material, as for example on infusion cannulas used for children, these wings are large in relation to the body portion of the catheter unit, implying that they will be in the way of the user's fingers when he grasps the infusion cannula in order to make the puncture, thus detracting from the accuracy of the operation and causing a risk of infection. Furthermore, such small catheter units frequently do not have the finger grip of larger catheter units, by means of which and a finger grip on the puncture unit, the assembly comprising the catheter and puncture units, i.e. the infusion cannula assembly, is manipulated for insertion in the vein and subsequent separation of the puncture unit from the catheter unit, the needle of which remains in the vein. Small catheter units do not have these finger grips, partly for manufacturing reasons, partly because large projections on the catheter unit, after puncture, might get entangled in bed clothes or the like. The desire to avoid such inconvenience also in connection with larger catheter units must give way to the great practical importance of the finger grip to the accurate puncture and subsequent neat separation of the puncture unit from the catheter unit.

It is the object of the present invention to provide, for catheter units equipped with wings and intended for infusion cannulas, an arrangement affording finger-grip function and keeping the attachment wings away from the user's fingers when vein puncture is effected.

According to the invention, this is achieved by means of an arrangement having the characteristic features stated in the appended claims. Thus, according to the invention the wings are used as an attachment for a removable sleeve serving as a finger-grip means and reducing the spread of the wings upon vein puncture and thus the risk that the user's fingers will touch the wings. The reduced spread of the wings has the further advantage that the infusion cannula can be accommodated in a smaller package, involving lower costs for transport and storing of cannulas. Another advantage is that the arrangement, owing to its wing-gripping function, prevents the wings from coming into contact with the patient's skin during vein puncture and thus does not have the braking effect on the puncture operation encountered with conventional wing arrangements. After the puncture operation it allows a safe guiding of the catheter unit for further insertion of the catheter tube into the vein and neat separation of the puncture unit from the catheter unit also with small infusion cannulas. After these manipulations the sleeve is removed from the catheter unit which thus does not have the tendency of conventional catheter units provided with projecting finger grips to get entangled in bed clothes and like objects after catheterisation. A further advantage of the arrangement according to the invention is that it makes for greater latitude in the design of the finger-grip surface and its location on the catheter unit.

An embodiment of the invention will be described in detail below, reference being had to the accompanying drawings in which FIG. 1 shows a conventional catheter unit with wings;

Figure 1:
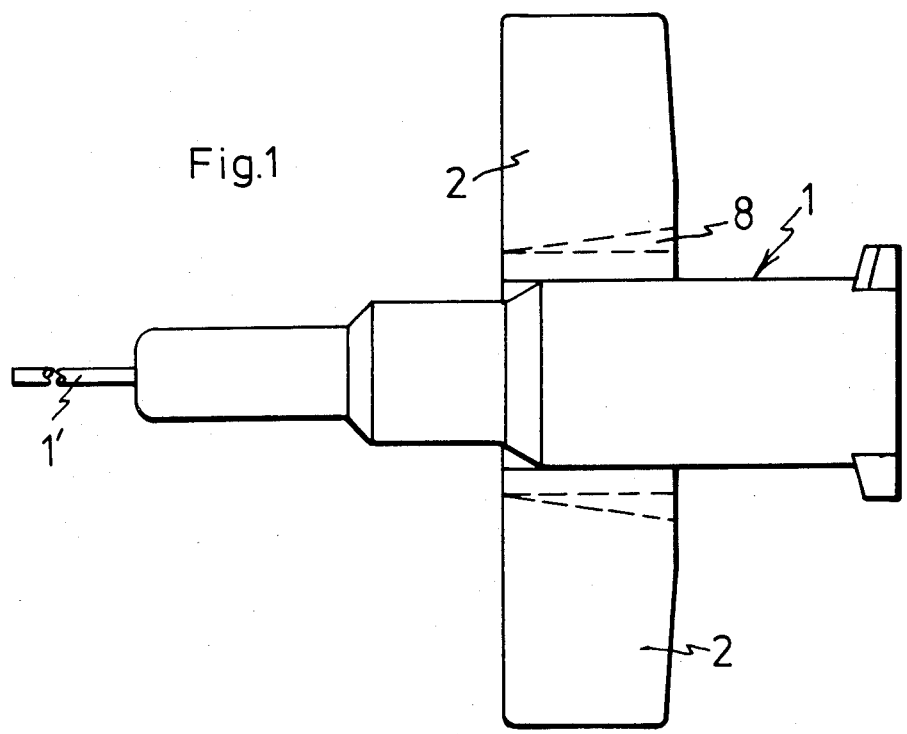
Figure 4:
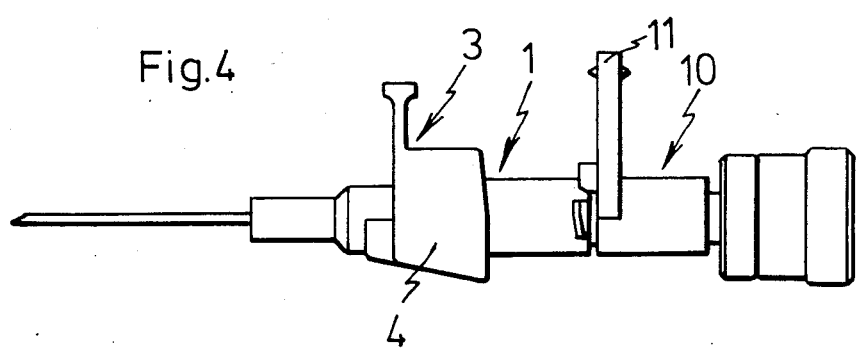
FIG. 4 shows an infusion cannula where the catheter unit is equipped with the arrangement according to the invention.
Figure 2:
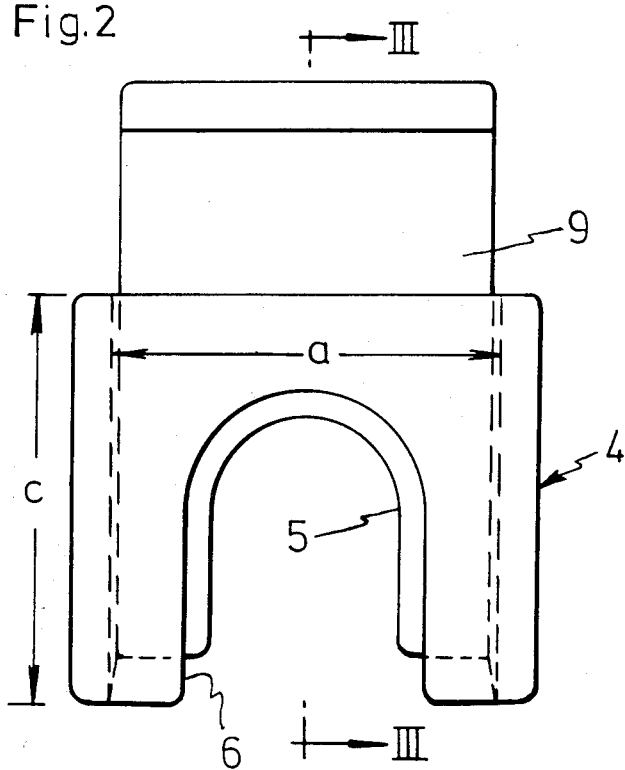
FIG. 2 is a rear view of a finger-grip and wing-folding sleeve in the arrangement according to the invention.
Figure 3:
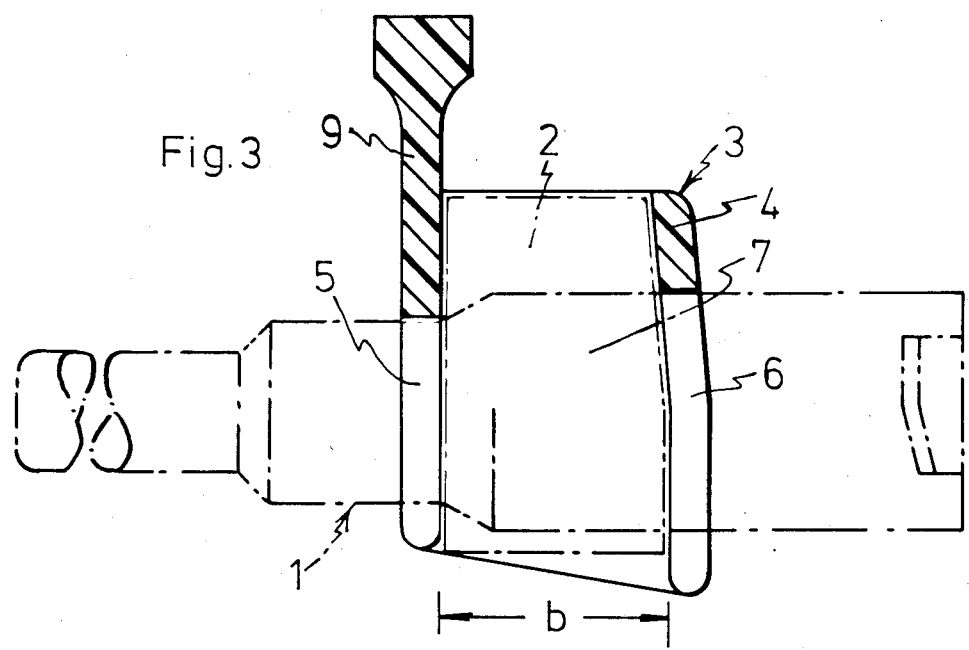
FIG. 3 is a view along line III—III in FIG. 2, the sleeve being mounted on a catheter unit shown by a broken line.

FIG. 1 shows a conventional catheter unit having a catheter tube 1' and attachment wings 2 at its lower side and consisting of a relatively flexible plastic material. The catheter unit is provided with a finger-grip and wing-folding means 3 according to the invention, in the manner shown in FIGS. 3 and 4. In the embodiment shown in FIGS. 2 to 4 the means 3 comprises a square plastic sleeve 4 formed in two opposed walls, the front wall and the rear wall, with an arched gate 5, 6, each of which has a width which is slightly larger than the diameter of the catheter unit body portion 7 on either side of the wings 2. The inner dimension of the sleeve 4 between the gates 5, 6 is slightly larger than the width of the wings 2, i.e. the wing dimension in the longitudinal direction of the catheter unit 1, and the inner width dimension of the sleeve, i.e. the dimension in the transverse direction of the catheter unit, is slightly larger than the sum of the diameter of the body portion between the wings and the double wing thickness. Bearing these dimensions of the sleeve in mind, it will be obvious that, after the wings of the catheter unit have been folded upwardly—for which purpose the points of connection between the wings and the body portion 7 of the catheter unit may have a scoring 8—the sleeve can, with the gate bases facing the wing tips, be pushed with a sliding fit over the catheter unit portion carrying the wings, such that the sleeve protectingly encloses the wings 2 and the edges of the gates embrace the body portion 7 of the catheter unit ahead of and behind the wings. The said sliding fit should be a close fit to make the wings 2 firmly support the sleeve on the catheter unit. The height of the sleeve is preferably at least of the same dimension as the length of the wings (i.e. the length of one wing), and the front wall 9 of the sleeve, i.e. the wall facing the cannula tip, is high enough to constitute a finger (index finger) grip upon manipulation of the infusion cannula according to FIG. 4. Normally, the height of this front wall is chosen such that its upper end is approximately on a level with the upper end of the thumb grip 11 on the puncture unit 10 of the infusion cannula when the sleeve has been pushed over the wings and the arched edges of the gates 5, 6 have been brought into engagement with the catheter unit body portion 7.

After the normal manipulations, i.e. vein puncture, positive insertion of the catheter tube 1' into the vein and separation of the puncture unit 10 from the catheter unit 1, have been carried out by means of the finger grips 9, 11, the sleeve 4 is removed from the catheter unit and the wings 2 are unfolded and then fixed to the skin of the patient in normal manner.

It will be appreciated that the embodiment described may be modified within the scope of the invention. For example, instead of the outer side of the sleeve front wall 9, the inner side of the sleeve rear wall may form the (index) finger grip on the catheter unit, in which case the rear wall should be higher than or extend beyond the front wall, and the sleeve may be more like a ring and enclose the wings over a distance less than the total wing height. Furthermore, the sleeve may be open, i.e. C-shaped in all cross-sections.

What we claim and desire to secure by Letters Patent is:

1. A catheter unit including a puncture unit, said catheter unit being in contact and associated with the puncture unit, the said puncture unit having a thumb grip to facilitate use of the catheter unit, said catheter unit consisting of an elongated body (7) and a means for mounting an infusion cannula, there being provided over said catheter body a sleeve formed of a central portion, a U-shaped front wall and a U-shaped rear wall, said front wall and said rear wall having arc shaped gates in each somewhat larger than the diameter of the catheter to permit the sleeve to fit over said catheter in a sliding fit, said gates having parallel fixed legs extending tangentially to said arc, the wings of said catheter being folded up and under the sleeve portion, the sleeve being open underneath.

2. A removable sleeve adapted for holding a catheter unit for infusion cannulas comprising a sleeve (4) having a front U-shaped wall (5) and a rear U-shaped wall (6) opposite each other and connected to each other by a connecting body portion, each of said front wall and rear wall having formed therein an arc shaped gate (5, 6) with parallel fixed legs extending tangentially to said arc, said gate being open at the bottom and having a width which is dimensioned so as to accommodate the diameter of a catheter unit, the distance between the inner surface of the said front wall and rear wall being such as to accommodate the wings of a catheter unit, a finger grip for manipulation extending from the top most portion of said connecting body portion in a direction opposite to the legs of said gates, said connecting body portion being open underneath and adapted to enable said sleeve to be placed over the top of a catheter unit.

3. The device as defined in claim 2 further comprising wherein the dimension of the connecting body portion of the sleeve (4) between the gates (5, 6) is greater than the width of any wings located on a catheter which may be used therewith.

4. The device as set forth in claim 2 further comprising wherein the dimension in the transverse direction of said sleeve is adapted to receive the body portion of a catheter having its wings folded in an upward manner.

5. The device as set forth in claim 2 wherein the finger grip extends above the front of the connecting body portion of the sleeve.

6. The device as set forth in claim 2 wherein the finger grip comprises an extension of the front of said sleeve and has the same width as said front wall and is provided with an essentially flat top and arcuate sections at the proximate end thereof to enable fingers to grip the device in a convenient manner.

7. The device of claim 2 wherein the rear wall extends below the lower end of the front wall and where the top edge of said rear wall is level with the connecting body portion of the sleeve.

8. The device of claim 6 wherein said rear wall is wider than said front wall.

9. The device of claim 2 which is made of plastic.

10. A catheter unit for infusion cannulas comprising a body portion (7) provided on either side with attached wings (2) folded against said body portion, said unit and folded wings being enclosed by a removable sleeve formed of a front U-shaped wall (5) and a rear U-shaped wall (6) opposite each other and connected to each other by a connecting body portion, each of said front wall and rear wall having formed therein an arc shaped gate (5, 6) with parallel fixed legs extending tangentially to said arc, said gate being open at the bottom and having a width which is dimensioned so as to accommodate the diameter of a catheter unit, the distance between the inner surface of the said front wall and rear wall being such as to accommodate the wings of a catheter unit, a finger grip for manipulation extending from the top most portion of said connecting body portion in a direction opposite to the legs of said gates, said connecting body portion being open underneath and adapted to enable said sleeve to be placed over the top of a catheter unit.

11. The catheter unit of claim 10 wherein the wings are made of flexible material permitting them to be folded in an upward direction to fit up and underneath the top portion and side portion of the sleeve device.

12. A method for holding a catheter unit while manipulating the unit including an infusion cannula for puncturing a blood vessel comprising associating a catheter unit with a puncture unit, said puncture unit being provided with a thumb grip, placing a sleeve device over the top of said catheter unit, the wings of said catheter unit being folded up underneath said sleeve, said sleeve device comprising a central body portion, a U-shaped front wall portion facing the infusion cannula and a U-shaped rearward wall facing the puncture unit, therebeing arc shaped gates formed in said front wall and said rear wall of a dimension to fit over the catheter unit having its wings folded up and underneath the sliding device, said gates having parallel fixed legs extending tangentially to said arc, therebeing an extension above the surface of the central body of said sleeve in a direction opposite to the legs of the gates to provide a finger grip to be used in association with the thumb grip to ensure proper advancement of the cannula and operation of the unit, thereafter manipulating the infusion cannula for vein puncture and then removing said sleeve device for reuse.

* * * * *